United States Patent [19]

Davis et al.

[11] Patent Number: 5,049,071
[45] Date of Patent: Sep. 17, 1991

[54] DENTAL SYRINGE TIP AND ADAPTOR

[76] Inventors: Warren Davis, 3026 Sullivan Ave., Rosemead, Calif. 91770; David Wasserman, 2095 Mohigan Way, Las Vegas, Nev. 89109

[21] Appl. No.: 351,431

[22] Filed: May 12, 1989

Related U.S. Application Data

[63] Continuation-in-part of Ser. No. 241,081, Sep. 6, 1988.

[51] Int. Cl.⁵ .............................................. A61G 17/02
[52] U.S. Cl. .................................. 433/80; 285/133.1; 222/145; 604/264; 604/283
[58] Field of Search .................... 433/80, 126; 604/43, 604/45, 150, 264, 275, 283, 243, 241, 902, 905; 128/207.14; 285/133.1, 137.1; 138/44, 109; 222/144.5, 145, 135

[56] References Cited

U.S. PATENT DOCUMENTS

| | | | |
|---|---|---|---|
| 2,460,473 | 2/1949 | Smith | 604/43 |
| 3,581,399 | 6/1971 | Dragan | 433/90 |
| 3,593,423 | 7/1971 | Jones | 433/80 |
| 3,727,310 | 4/1973 | Baker | 433/80 |
| 3,771,527 | 11/1973 | Ruisi | 604/43 |
| 3,874,083 | 4/1975 | Buckley | 433/80 |
| 4,026,025 | 5/1977 | Hunt | 433/80 |
| 4,248,589 | 2/1981 | Lewis | 433/80 |
| 4,531,913 | 7/1985 | Taguchi | 433/80 |
| 4,619,612 | 10/1986 | Weber | 433/80 |
| 4,648,871 | 3/1987 | Jacob | 604/45 |

FOREIGN PATENT DOCUMENTS

| | | | |
|---|---|---|---|
| 1283435 | 11/1968 | Fed. Rep. of Germany | 433/80 |
| 3526579 | 7/1986 | Fed. Rep. of Germany | 433/80 |

OTHER PUBLICATIONS

ADEC Publication, installation instructions autoclavable syringe tip kits (one page).

*Primary Examiner*—Gene Mancene
*Assistant Examiner*—Adriene B. Lepiane
*Attorney, Agent, or Firm*—Quirk, Tratos & Roethel

[57] ABSTRACT

A clear rigid plastic syringe tip having a central water passageway and three arcuate section air passageways disposed circumferentially about the water passageway. The syringe tip has an extension that mounts the syringe tip into an adaptor which holds the assembly in the handpiece body. Alternatively, the adaptor is provided with a coupling device for joining the syringe tip to the adaptor.

56 Claims, 4 Drawing Sheets

DENTAL SYRINGE TIP AND ADAPTOR

CROSS REFERENCE TO RELATED APPLICATION

This application is a Continuation-in-Part of Application Ser. No. 07/241,081, filed Sept. 6, 1988, entitled "Dental Syringe Tip and Adaptor".

BACKGROUND OF THE INVENTION

This invention relates to dental syringe tip assemblies, and more particularly to dental syringe tip assemblies having a disposable tip and an innovative adaptor.

For the past twenty-five years, dentists have been using a three-way syringe. An air tube and a water tube join together at the handpiece. Two operating buttons are provided on the handpiece body to allow activation by the dentist of the air or water. By depressing the air button, air flows out of the tip into the appropriate area of the patient's mouth to dry the field of operation. By depressing the water button, a passive flow of water is emitted to clean and float away debris and congestion from the field of operation. By depressing both buttons simultaneously, a spray of air and water is emitted which flushes away debris which can then be vacuumed from the oral cavity. Typical of a three-way syringe assembly is that shown in U.S. Pat. No. 3,874,083 to Buckley.

During these twenty-five years, there has only been one significant improvement made to this essential piece of dental equipment. In approximately 1979, the tip of the syringe was made removable to allow for sterilization. Before 1979, tips were disinfected and cleaned by simply wiping them with alcohol. With the development of the removable tip, sterilization of each tip could be accomplished through the use of steam or chemical heat procedures. However, if done with the appropriate frequency, the tip becomes clogged and unusable in several months. This is due to minerals and other impurities in the steam used in an autoclave which causes alkaline and calcium deposits to build up in the orifices of the tip which interrupt the flow of air and water from the tip. The air and water orifices in the tip are quite small, so that any irregularities occurring during fabrication will also decrease the life expectancy of the tip. Any plugging of the tip orifices results in both a loss of spray pressure as well as a loss of spray accuracy. Tips are conventionally made out of metal and it would be cost prohibitive to discard a metal tip after only a single use.

With the rising incidence of communicable diseases such as hepatitis and acquired immune deficiency syndrome, extreme care must be taken to prevent the transmission of germs (viral or bacterial) from one patient to the next. With the conventional metal tips, it is necessary to sterilize the tip after each patient use. This is due to a condition that occurs in the end of the tip during use known as water retraction (also called suck-back or draw-back), which is a negative pressure applied to the water line. In a syringe, water retraction is used to prevent siphoning or dripping from the water line. When water retraction occurs, water, saliva and blood from the patient's mouth can be drawn back into the end of the tip and then passed on to the next patient. This provides the opportunity for the transfer of infection from one patient to the next. Also, latent bacterial growth can be promoted in both the tip and the entire water system lines because of the existence of this potentially contaminating material. Both the Center for Disease Control and the American Dental Association recommend that water lines be non-retracting. To further mitigate this possibility of cross-contamination from one patient to the next, the routine sterilization of handpieces as well as air/water syringes is desirable. In the case of handpieces and air/water syringes that cannot be sterilized, it is recommended that other complete cleaning and disinfection procedures be followed.

A disposable syringe tip is disclosed in U.S. Pat. No. 4,026,025 to Roderick S. Hunt. The plastic tip is disclosed as flexible and can be easily bent by hand without any special tools or heating. Such a flexible tip would suffer from the limitation that it would not function as a retractor. It is necessary when applying air, water or a spray to the patient's mouth to be able to use the syringe tip as a retractor to move the patient's tongue, cheeks or lips. If the syringe tip were flexible, it would fail to perform this important retraction function.

The syringe tip and mounting collet disclosed in the Hunt patent also have further design limitations. The chamfered surface on the end of the syringe tip effectively directs the air away from the water thereby impeding the formation of the water spray which is so important in a three-way syringe. The small circular air passages further limit the amount of air exiting the end of the tip and these air passages would be subject to being crimped closed when the flexible tip is bent. The syringe tip is press fit on the end of a small nipple on the collet in such a manner that the air and water pressure leaving the handpiece body and entering the syringe tip would lead to a loosening of the press fit thereby causing the syringe tip to dislodge from the nipple. This design is also not adaptable to most three-way piece syringe assemblies on the market.

It is an object of the present invention to alleviate the transmission of germs (viral or bacterial) which cause infection or disease, from one patient to the next, and to eliminate the need to resterilize a syringe tip after each use.

It is a feature of the present invention to provide a clear, plastic disposable rigid syringe tip that is discarded after its use on a single patient, as well as to provide a novel adaptor to connect the disposable syringe tip to the handpiece body.

It is an advantage of the present invention that a more sterile dental environment will be created as well as the flow of air, water or spray from the syringe to the oral cavity will be improved.

Other objects, features and advantages will become apparent when the detailed description and drawings of the present invention are considered.

DETAILED DESCRIPTION OF THE PREFERRED EMBODIMENTS

Figure 1:
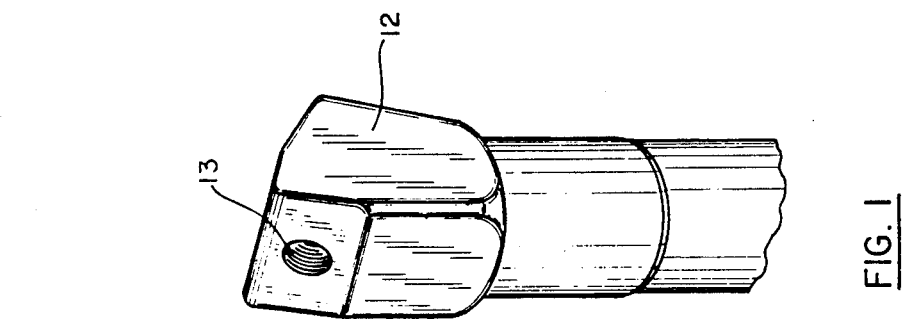
FIG. 1 shows an exploded view of a dental syringe assembly incorporating the present invention.

A dental syringe assembly 10 includes a conventional handpiece body 12 on which is mounted a syringe tip 14. The tip 14 is an elongated cylindrical member preferably made of a rigid plastic material. The tip 14 is provided with a bend 17, at preferably an angle of approximately 30°, to provide easy access to any portion of the patient's mouth during use of the syringe assembly. An adaptor 20 screws into a threaded opening 13 in the handpiece body 12 and is sealed toward one end of the adaptor by a first rubber O-ring 16. A second rubber O-ring 22 provides a seal at the midpoint of the adaptor 20.

The tip 14 is press fit onto a tapered male connector 21 (see FIGS. 7 and 8) that is mounted axially in the interior of the adaptor 20. A collet 26 and a third O-ring 24 provide a seal for the tip 14—male connector 21 assembly. A nut 28 comprises a locking assembly and screws onto the threads 44 on the outer surface of adaptor 20 to secure the tip 14, collet 26 and third O-ring 24 in place. Each of these parts, other than the specific tip 14 and the specific adaptor 20, are the conventional assembly for a three-way syringe tip assembly such as Model No. 23-0090-00 or Model No. 90-0125-00 sold by the Adec Corporation of Newberg, Oreg. or the DCI 3-way syringe sold by Air-Con Inc. of Portland, Oreg.

The tip 14 is shown in detail in FIGS. 2 through 6. The tip 14 is designed to be disposable after a single use. The tip material is fabricated in a single-step extrusion process, and is made from any rigid transparent plastic. A rigid plastic is preferred to fulfill the need to use the tip for continued retraction of the cheek and tongue by the dental operator. In a preferred embodiment, the tip 14 is made from a polycarbonate plastic, nylon or other rigid plastic materials. Suitable rigid plastic transparent material is that sold by General Electric Co. under the trademark Ultem 1000 or that sold by Victrex Corp. under the trademark Peek.

As shown in FIGS. 2 through 6, a central water passageway 32 runs the entire length of the tip 14 and is used to deliver water from the handpiece body 12 to the patient's mouth. Three air passageways 34 also run the entire length of the tip 14, are disposed circumferentially about the central passageway 32 and are used to deliver air from the handpiece body 12 to the patient's mouth. If both air and water are delivered through the tip 14 simultaneously, a spray results at the exit end 15 of the tip 14.

In a preferred embodiment, the elongated cylindrical member comprising tip 14 has a diameter in a range generally of 0.140"–0.150", and most preferably has a diameter of approximately 0.145". The water passageway 32 has a diameter in a range of generally 0.035"–0.039", and most preferably has a diameter of approximately 0.036". Each air passageway 34 comprises in cross-section an arcuate section (see FIG. 3) approximately one-third of the circumference of the tip 14. Each arcuate section has a width in a range of generally 0.016"–0.020", and preferably has a width of approximately 0.017". The arcuate sections are separated from one another by thin support segments 38, each having a thickness of approximately 0.018".

Figure 3:
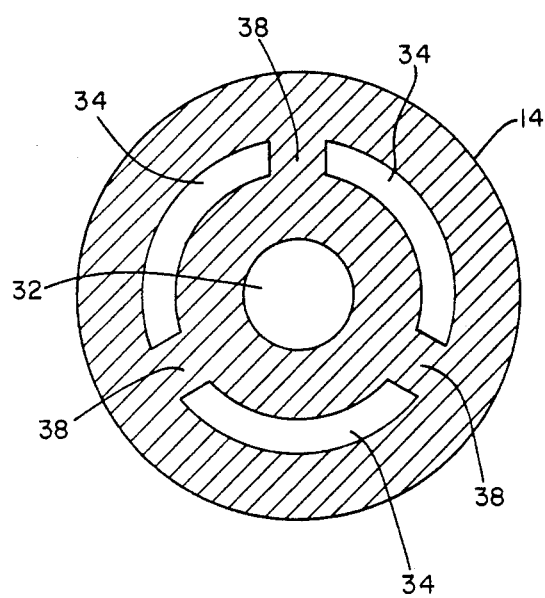
FIG. 3 shows a cross-section taken along line 3—3 of FIG. 2 of the disposable syringe tip of the present invention.

While the air passages 34 shown in FIG. 3 are shown in cross-section as an arcuate section, other cross-sectional shapes can also be used such as rectangular sections, triangular sections and elliptical sections. Likewise, the central water passageway 32, shown in FIG. 3 as having a circular cross-section, can alternatively have other cross-sections such as square, rectangular, elliptical or triangular.

The support segments 38 are also shown in FIG. 3 as being symmetrically oriented about the circumference of the tip 14 approximately 120°±4" apart. It is also possible to asymmetrically orient the support segments 38 about the circumference of the tip which would result in some of the air passages 34 being longer in cross-section than others. Also, while three support segments 38 are shown, as few as two or as many as four or more support segments can also be used.

Figure 4:
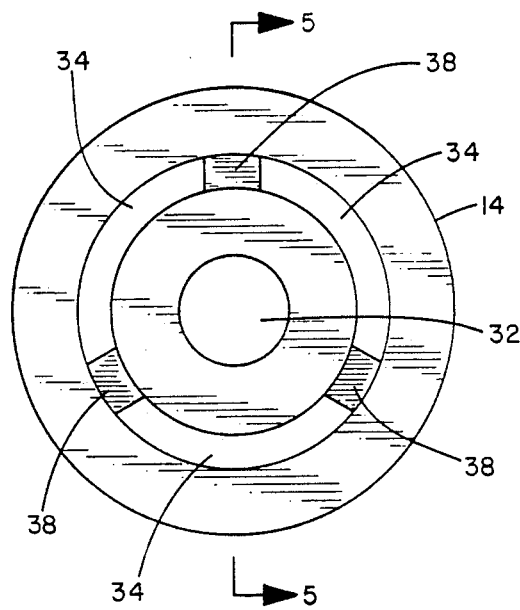
FIG. 4 shows an end view taken along line 4—4 of FIG. 2 of the exit end of the disposable syringe tip of the present invention.
Figure 5:
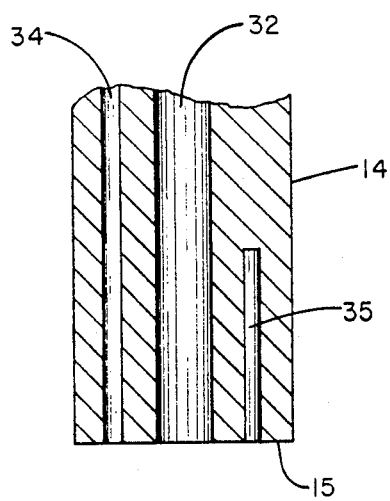
FIG. 5 shows a cross-section of the exit end of the disposable syringe tip taken along line 5—5 of FIG. 4.
Figure 6:
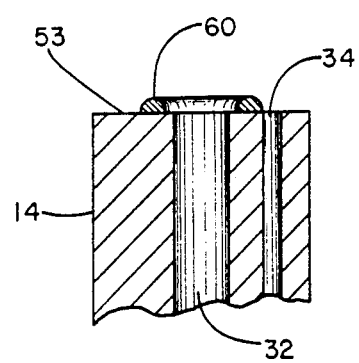
FIG. 6 shows a cross-section of the entrance end of the disposable syringe tip taken along lines 6—6 of FIG. 2.

As shown in FIGS. 4 and 5, at the exit end 15 of the tip 14, the air passages 34 combine to form a continuous 360° annulus 35 around the water passage 32. This can be achieved during the fabrication of the tip 14 by die-cutting to the desired depth each support segment 38 inward from the exit end 15 of the tip 14. While die-cutting is the preferred way of forming the continuous annulus 35, other methods can be used to remove the support segments 38 to the desired depth. In the preferred embodiment, the depth of the continuous annulus 35 from the exit end 15 of the tip 14 inward is approximately 0.125".

The continuous annulus 35 achieves a quite effective mixing of the air and water which results in a uniform spray which is easily directed by the dental operator at the needed locations in the patient's mouth.

Figure 7:
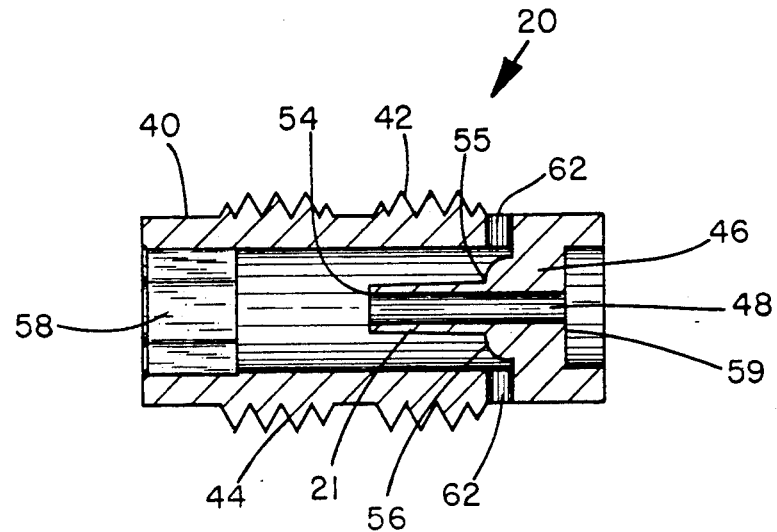
FIG. 7 shows in section the adaptor of the present invention.
Figure 8:
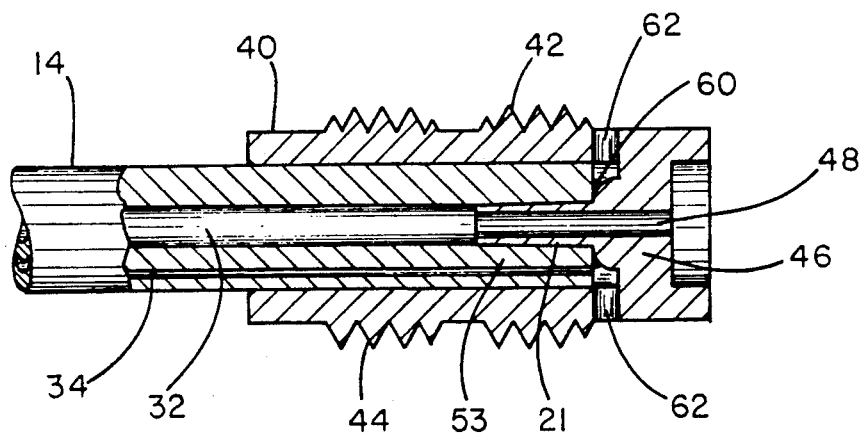
FIG. 8 shows the adaptor with a portion of the syringe tip mounted thereon.

FIGS. 7 and 8 show the adaptor 20 that is used to connect the tip 14 to the handpiece body 12. The adaptor 20, preferably made of metal, comprises a generally cylindrical body having a hollow interior. The exterior wall 40 of the adaptor 20 has a first set of threads 42 for attaching the adaptor 20 to the threaded opening 13 in the handpiece body 12. A baffle 46 extends across the hollow interior of the cylindrical adaptor 20. Formed integrally with the baffle 46 is a male connector 21 formed as a cylindrical member and having an axial opening 48 therethrough. The male connector 21 is tapered to receive the entrance end 53 of the tip 14. The male connector 21 is also formed of metal and has an outer diameter at its forward end 54 of approximately 0.032" and tapers out at its bottom end 55 to a diameter of approximately 0.038. The male connector 21 is press fit into the water passageway 32 of the end 53 of the tip 14. A rounded shoulder 56, which surrounds the bottom of the male connector 21 at the location where the male connector 21 joins the baffle 46, cooperates with a resilient O-ring coating 60 on the entrance end 53 of the tip 14 (see FIG. 6) to form a seal to prevent water from leaking. Alternatively, the resilient O-ring coating 60 can be omitted from the entrance end 53 of the tip 14 without significantly decreasing the water-tightness of the connection between the tip 14 and the male connector 21. The baffle 46 communicates at 59 through axial opening 48 with a water line by way of a valve (not shown) in the handpiece body 12.

A plurality of circumferentially arranged channels 62 in the cylindrical body provide openings to allow the air from the handpiece body 12 to pass to the hollow interior of the adaptor 20 and then into the air passageways 34.

A second set of threads 44 is provided on the exterior wall 40 of the adaptor 20. These threads 44 cooperate with the threads in nut 28 to seal the tip 14 to the adaptor 20.

The forward interior portion of the adaptor 20 is provided with an hexagonal cross-section 58 which allows the use of an allen wrench to screw the adaptor 20 into the opening 13 in the handpiece body 12.

The present invention yields significant advantages over the syringe tip-adaptor assemblies used previously. By using a disposable syringe tip, a source of infection and cross-contamination of micro-organisms from one patient to the next is eliminated. When a three-way syringe is used, back pressure is created at the end 15 of the syringe tip 14 whenever the air and water flow is abruptly cut off. This back pressure can cause contaminated water, saliva or blood to be drawn back into the tip openings. If the tip 14 were to be used on a second patient, any micro-organisms in the contaminated water, saliva or blood from the first patient could infect the second patient. A disposable tip 14 used for each patient eliminates this problem.

Existing metal tips should be sterilized prior to use using an autoclave sterilization system. The disposable tip eliminates the need for this autoclave sterilization equipment. Each tip 14 is sanitary during the manufacturing process and is then packaged. A dentist selects a packaged tip, removes the tip from its package or visually inspects the tip if it is already installed. The clear rigid plastic material from which the tip is made allows visual verification of the tip's sanitary state. If sterilization is required, such can be achieved during the manufacturing process by using any suitable sterilization process, such as gamma ray sterilization.

The prior art metal tip comprised two concentric tubes—an inner water tube surrounded by an outer air tube. In practice, the orifice at the end of the prior art metal tip can be quite irregular causing uneven spray when the air and water flows are effected simultaneously. Uneven flows results in an unpredictable spray pattern.

The extruded tip 14 of the present invention yields very uniform orifices for both air and water at the end 15 of the tip 14. This results in a uniform distribution of air, water or spray. A continuous, uninterrupted air supply through parallel air passageways 34 mitigates air turbulence and therefore produces a more accurate and controlled spray.

The adaptor 20 is different from the prior art adaptors. The tapered male connector 21 with the axial opening 48 provides a mounting location for the tip 14 and keeps the water supply separate from the air supply until they are mixed together at the end 15 of the tip 14 to form the spray. When the air and water are activated simultaneously by the dental operator, the continuous 360° air annulus 35 around the central water passage 32 combines to produce a fine spray.

Figure 9:
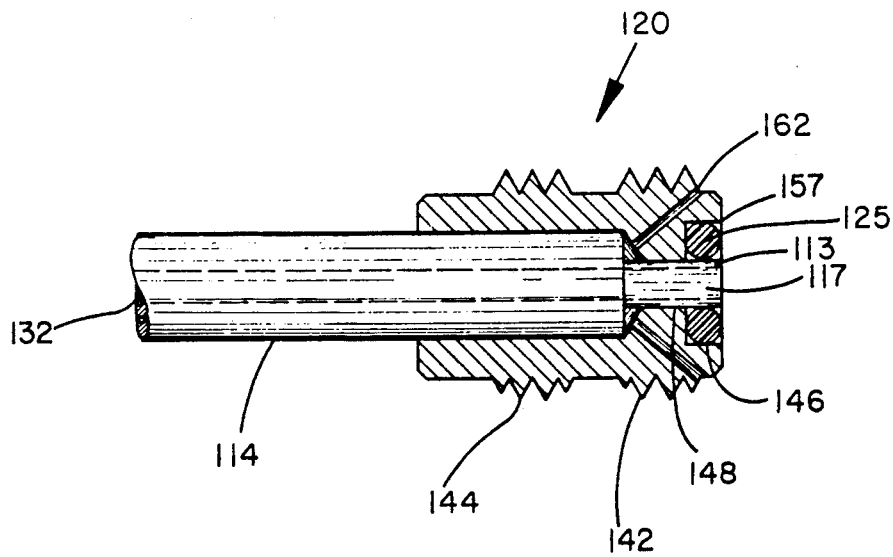
FIG. 9 shows in partial cross-section an alternate embodiment of the syringe tip and adaptor of the present invention.

An alternate embodiment of the present invention is shown in FIG. 9. The adaptor 120 is a conventional adaptor used in a conventional all-metal dental syringe assembly. The adaptor 120 has a first set of threads 142 for attaching the adaptor 120 to the threaded opening 13 in the handpiece body 12 (FIG. 1). The adaptor 120 has a second set of threads 144 which cooperate with the threads in nut 28 (FIG. 1) to seal the tip 114 to the adaptor 120. A plurality of circumferentially-disposed channels 162 (only one shown) are provided in the body of the adaptor 120 to allow air from the handpiece body 12 to pass to the hollow interior of the tip 114.

Figure 2:
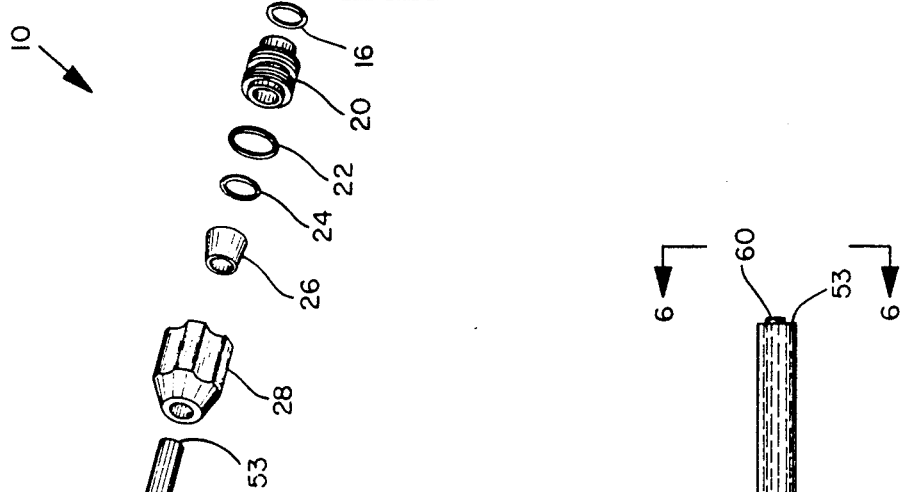
FIG. 2 shows a disposable syringe tip of the present invention.

The syringe tip 114 is similar to the tip 14 shown in FIGS. 2-4. The tip is fabricated from rigid plastic material and has the same internal cross-section configuration shown in FIGS. 3 and 4. The tip 114 has a tip extension 113 formed integrally with the tip 114 at the entrance end of the tip 114. The tip extension 113 extends through an axial opening 148 in a baffle 146 that extends across the interior of the adaptor 120. The adaptor 120 at its end 157 has an insert portion to accommodate an annular rubber sealing ring 125 that surrounds the tip extension 113.

In the preferred embodiment, the outer diameter of the tip extension 113 is in the range generally of 0.062"-0.066", and most preferably is approximately 0.064". The length of the tip extension 113 is in the range generally of 0.012"-0.032", and most preferably has a length of approximately 0.022".

The tip extension 113 has a hollow central channel 117 that allows water from the handpiece body 12 to pass into the central passageway 132 of the tip 114.

Figure 10:
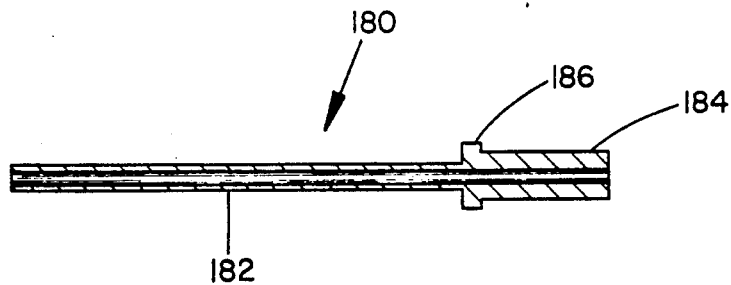
FIG. 10 shows in cross-section a coupling device used in an alternate embodiment of the present invention.

FIG. 10 shows in cross-section a coupling device 180 used in connection with an alternate embodiment of the present invention. The coupling device 180 comprises a mounting stem 184 having an expanded shoulder 186 and an interior hollow member 182.

Figure 11:
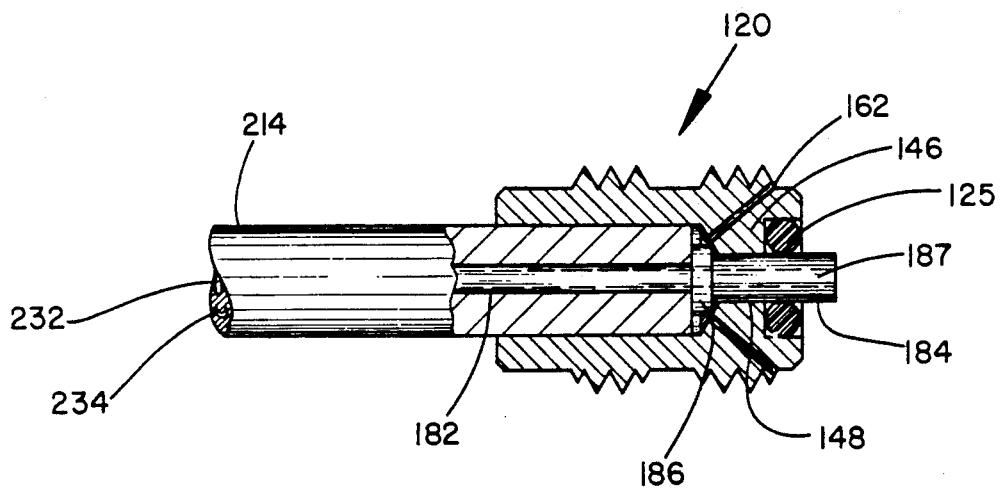
FIG. 11 shows in partial cross-section the syringe tip-coupling device-adaptor assembly of an alternate embodiment of the present invention.

The coupling device 180 in use is shown in FIG. 11. A conventional adaptor 120 (having the same elements as described with reference to FIG. 9) has a coupling device 180 mounted therein. The mounting stem 184 of the coupling device 180 is positioned in the axial opening 148 of the baffle 146 and is held in place by an annular rubber sealing ring 125. The expanded shoulder 186 of the coupling device 180 fits against the interior wall of the baffle 146. A plastic syringe tip 214 is press fit onto the interior hollow tip member 182 of the coupling device 180. Water from a handpiece body 12 is directed down the hollow passageway 187 in the coupling device 180 to the central passageway 232 of the tip 214. The expanded shoulder 186 does not block the air passageway 162 that provides air to the air passageways 234 in the tip 214.

In the preferred embodiment, the overall length of the coupling device 180 is in the range of generally 0.815"-0.835", and most preferably has a length of approximately 0.825". The coupling device 180 has a mounting stem 184 that has a length in the range of generally 0.165"-0.185", the expanded shoulder 186 has a length in the range generally of 0.020"-0.030" and the hollow tip member 182 has a length in the range generally of 0.615". In the most preferred embodiment, the mounting stem has a length of approximately 0.175", the expanded shoulder has a length of approximately 0.025" and the hollow tip member has a length of approximately 0.625". The hollow tip member 182 may be slightly tapered to assist its insertion into the end of the tip 214.

Other advantages inure from the use of plastic as the material from which the tip 14 is fabricated. A plastic tip will transmit less heat and cold to sensitive tissues in the oral cavity. Plastic tips are not electrically conductive and will not transmit a spark which can occur during modern dental treatments using electro-surgical devices. Also plastic tips are not harmed by the presence of ultrasonic devices.

The tip 14 is fabricated from a good quality, rigid plastic. The bend 17 in the tip 14 is provided during a heat forming step and once the plastic has cooled, the bend is a permanent part of the rigid tip 14. The entire tip fabrication process including extruding the plastic with the central water passage 32 and the arcuate section air passages 34, cutting the plastic extrusion to length, heat forming the bend 17, die-cutting the continuous 360° air annulus 35 and forming the resilient O-ring seal 60 is performed in a special multiple operation machine.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

We claim:

1. A syringe tip comprising an elongated cylindrical rigid plastic member having a first central passageway throughout the entire length of the cylindrical member, said first central passageway being generally circular in cross-section, and a plurality of second passageways disposed circumferentially about the first central passageway, said second passageways being generally arcuate in cross-section and extending substantially the entire length of the tip, and a syringe tip extension having an interior passageway for joining the syringe tip to an adaptor.

2. The syringe tip of claim 1 wherein the cylindrical member has a diameter in the range generally of 0.140"–0.150".

3. The syringe tip of claim 2 wherein the cylindrical member has a diameter of approximately 0.145".

4. The syringe tip of claim 1 wherein the first central passageway has a diameter in a range of generally 0.035"–0.039".

5. The syringe tip of claim 4 wherein the first central passageway has a diameter of approximately 0.036".

6. The syringe tip of claim 1 wherein each second passageway has a width in a range of generally 0.016"–0.020".

7. The syringe tip of claim 6 wherein each second passageway has a width of approximately 0.017".

8. The syringe tip of claim 1 wherein a thin support segment separates each second passageway from one another.

9. The syringe tip of claim 8 wherein the thin support segment has a thickness of approximately 0.018".

10. The syringe tip of claim 1 wherein the plurality of second passageways combine to form a continuous annulus around the first central passageway at the exit end of the syringe tip.

11. The syringe tip of claim 10 wherein the depth of the continuous annulus is approximately 0.125".

12. The syringe tip of claim 1 wherein the elongated member has a bend along the length thereof.

13. The syringe tip of claim 12 wherein the bend has an angle of approximately 30°.

14. The syringe tip of claim 1 wherein the syringe tip extension is formed integrally with the elongated member at the entrance end of the tip.

15. The syringe tip of claim 1 wherein the outer diameter of the syringe tip extension is less than the outer diameter of the elongated member.

16. The syringe tip of claim 1 wherein the elongated member is made of a polycarbonate plastic.

17. The syringe tip of claim 16 wherein the elongated member is transparent.

18. The syringe tip of claim 1 wherein the elongated member is made of nylon.

19. The syringe tip of claim 18 wherein the elongated member is transparent.

20. The syringe tip of claim 1 wherein the elongated member is transparent.

21. The syringe tip of claim 1 wherein the first central passageway is a water passageway.

22. The syringe tip of claim 21 wherein the second passageway is an air passageway.

23. The syringe tip of claim 1 wherein the second passageway is an air passageway.

24. The syringe tip of claim 1 wherein the outer diameter of the syringe tip extension is in the range generally of 0.062"–0.066".

25. The syringe tip of claim 24 wherein the outer diameter of the syringe tip extension is approximately 0.064".

26. The syringe tip of claim 1 wherein the length of the syringe tip extension is in a range of generally 0.012–0.032".

27. The syringe tip of claim 26 wherein the length of the syringe tip extension is approximately 0.022".

28. A syringe tip assembly comprising
   a) a syringe tip comprising an elongated cylindrical rigid plastic member having a first central passageway throughout the entire length of the cylindrical member, said first central passageway being generally circular in cross-section, and a plurality of second passageways disposed circumferentially about the first central passageway, said second passageways being generally arcuate in cross-section and extending substantially the entire length of the tip.
   b) an adaptor means for mounting the syringe tip to a handpiece body, and
   c) a syringe tip coupling device comprising a mounting stem having an internal passageway for mounting the syringe tip coupling device to the adaptor means, an expanded shoulder on one end of the mounting stem and a hollow tip member having an internal passageway mounted to the expanded shoulder for mounting the syringe tip on the coupling device.

29. The syringe tip coupling device of claim 33 wherein the mounting stem has a length in a range generally of 0.165–0.185", the expanded shoulder has a length in a range generally of 0.020–0.030" inches and the hollow tip member had a length in a range generally of 0.615"–0.635".

30. The syringe tip coupling device of claim 29 wherein the mounting stem has a length of approximately 0.175", the expanded shoulder has a length of approximately 0.025" and the hollow tip member has a length of approximately 0.625".

31. A syringe tip assembly comprising:
  a) a syringe tip comprising an elongated cylindrical rigid plastic member having a first central passageway throughout the entire length of the cylindrical member, said first central passageway being generally circular in cross-section, and a plurality of second passageways disposed circumferentially about the first central passageway, said second passageways being generally arcuate in cross-section and extending substantially the entire length of the tip, and
  b) a syringe tip extension having an interior passageway mounted to the elongated member, and
  c) means for mounting the syringe tip and syringe tip extension to a handpiece body.

32. The syringe tip assembly of claim 31 wherein the means for mounting the syringe tip and syringe tip extension to a handpiece body comprises a syringe tip adaptor comprising
  a) a generally cylindrical body having a hollow interior,
  b) means for connecting the cylindrical body to the handpiece body,
  c) a baffle mounted within the hollow interior of the cylindrical body, and
  d) an axial opening in the baffle for receiving the syringe tip extension.

33. A syringe tip comprising an elongated cylindrical rigid plastic member having a first central passageway throughout the entire length of the cylindrical member, said first central passageway being generally circular in cross-section, and a plurality of second passageways disposed circumferentially about the first central passageway, said second passageways being generally arcuate in cross-section and extending substantially the entire length of the tip.

34. The syringe tip of claim 33 wherein the cylindrical member has a diameter in the range generally of 0.140"-0.150".

35. The syringe tip of claim 34 wherein the cylindrical member has a diameter of approximately 0.145".

36. The syringe tip of claim 33 wherein the first central passageway has a diameter in a range of generally 0.035"-0.039".

37. The syringe tip of claim 36 wherein the first central passageway has a diameter of approximately 0.036".

38. The syringe tip of claim 33 wherein each second passageway has a width in a range of generally 0.016"-0.020".

39. The syringe tip of claim 38 wherein each second passageway has a width of approximately 0.017".

40. The syringe tip of claim 33 wherein a thin support segment separates each second passageway from one another.

41. The syringe tip of claim 40 wherein the thin support segment has a thickness of approximately 0.018".

42. The syringe tip of claim 33 wherein the plurality of second passageways combine to form a continuous annulus around the first central passageway at the exit end of the syringe tip.

43. The syringe tip of claim 42 wherein the depth of the continuous annulus is approximately 0.125".

44. The syringe tip of claim 33 wherein the elongated member has a bend along the length thereof.

45. The syringe tip of claim 44 wherein the bend has an angle of approximately 30°.

46. The syringe tip of claim 33 wherein the elongated member has a resilient O-ring coating around the first central passageway at the entrance end of the tip.

47. The syringe tip of claim 33 wherein the elongated member is made of a polycarbonate plastic.

48. The syringe tip of claim 47 wherein the elongated member is transparent.

49. The syringe tip of claim 33 wherein the elongated member is transparent.

50. The syringe tip of claim 33 wherein the first central passageway is a water passageway.

51. The syringe tip of claim 50 wherein the second passageway is an air passageway.

52. The syringe tip of claim 33 wherein the second passageway is an air passageway.

53. A syringe tip assembly including
  a) a syringe tip comprising an elongated cylindrical rigid plastic member having a first central passageway throughout the entire length of the cylindrical member, said first central passageway being generally circular in cross-section, and a plurality of second passageways disposed circumferentially about the first central passageway, said second passageways being generally arcuate in cross-section and extending substantially the entire length of the tip, and
  b) means for mounting the syringe tip to a handpiece body.

54. The syringe tip assembly of claim 53 wherein the means for mounting the syringe tip to a handpiece body comprises a syringe tip adaptor comprising
  a) a generally cylindrical body having a hollow interior,
  b) first means for connecting the cylindrical body to the handpiece body,
  c) a baffle mounted within the hollow interior of the cylindrical body,
  d) a tapered male connector formed integrally with the baffle and having an axial opening therethrough whereby when a syringe tip is mounted on the tapered male connector, the syringe tip will be tightly held on the connector to prevent axial rotation of the syringe tip and to ensure that air and water from the passageways do not leak into each other, and
  e) a rounded shoulder surrounding the male connector at the location where the male connector meets the baffle to provide a sealing surface when the syringe tip is mounted on the male connector and to provide access for air to enter into air passageways in the syringe tip while at the same time preventing water from leaking out of a water passageway in the syringe tip.

55. A dental syringe assembly comprising a handpiece body including means for mounting a syringe tip assembly to the handpiece body, said syringe tip assembly comprising
  a) a syringe tip adaptor for connecting a syringe tip to the handpiece body, and
  b) a syringe tip comprising an elongated cylindrical rigid plastic member having a first central passageway throughout the entire length of the cylindrical member, said first central passageway being generally circular in cross-section, and a plurality of second passageways disposed circumferentially about the first central passageway, said second passageways being generally arcuate in cross-section and extending substantially the entire length of the tip.

56. A dental syringe assembly comprising a handpiece body including means for mounting a syringe tip assembly to the handpiece body, said syringe tip assembly comprising
   a) a syringe tip adaptor for connecting a syringe tip to a handpiece body comprising
      (1) a generally cylindrical body having a hollow interior,
      (2) first means for connecting the cylindrical body to the handpiece body,
      (3) a baffle mounted within the hollow interior of the cylindrical body,
      (4) a tapered male connector formed integrally with the baffle and having an axial opening therethrough, and
      (5) a rounded shoulder surrounding the male connector at the location where the male connector meets the baffle to provide a sealing surface when the syringe tip is mounted on the male connector, and
   b) a syringe tip mounted on the syringe tip adaptor, the syringe tip comprising an elongated cylindrical rigid plastic member having a first central passageway through the entire length of the cylindrical member, said first central passageway being generally circular in cross-section, and a plurality of second passageways disposed circumferentially about the first central passageway, said second passageways being generally arcuate in cross-section and extending substantially the entire length of the tip.

* * * * *